(12) United States Patent
Fitz et al.

(10) Patent No.: US 7,771,769 B2
(45) Date of Patent: Aug. 10, 2010

(54) FLAVOURING A FOODSTUFF BY INCORPORATING AN EFFECTIVE AMOUNT OF AT LEAST ONE COMPOUND OF THE FORMULA R1-S-R2 IN WHICH R1 AND R2 REPRESENT A SPECIFIC ATOM OR GROUP

(75) Inventors: Wolfgang Fitz, Amsterdam (NL); Josef Kerler, Naarden (NL); Harry Renes, Lelystad (NL); Nico Bouter, Blaricum (NL)

(73) Assignee: Quest International B.V., GP Naarden (NL)

( * ) Notice: Subject to any disclaimer, the term of this patent is extended or adjusted under 35 U.S.C. 154(b) by 1273 days.

(21) Appl. No.: 10/240,772

(22) PCT Filed: Apr. 5, 2001

(86) PCT No.: PCT/NL01/00279

§ 371 (c)(1),
(2), (4) Date: Sep. 16, 2003

(87) PCT Pub. No.: WO01/76390

PCT Pub. Date: Oct. 18, 2001

(65) Prior Publication Data

US 2004/0052914 A1 Mar. 18, 2004

(30) Foreign Application Priority Data

Apr. 6, 2000 (EP) .................................. 00201267

(51) Int. Cl.
*A23L 1/22* (2006.01)
(52) U.S. Cl. .................... 426/535; 426/534; 426/650
(58) Field of Classification Search .................. 426/534, 426/535, 650
See application file for complete search history.

(56) References Cited

U.S. PATENT DOCUMENTS

| 3,615,601 | A | 10/1971 | Brodnitz |
| 3,713,848 | A | 1/1973 | Katz |
| 3,879,562 | A | 4/1975 | Pittet et al. |
| 3,970,689 | A | 7/1976 | Stoffelsma et al. |
| RE30,370 | E | 8/1980 | Pittet et al. |
| 4,285,984 | A | 8/1981 | Huber |
| 4,631,194 | A | 12/1986 | Courtney et al. |
| 5,047,256 | A | 9/1991 | Bruijnje et al. |

FOREIGN PATENT DOCUMENTS

| DE | 19 18 056 | A | 11/1969 |
| EP | 1 247 829 | | 9/1971 |
| EP | 2 124 868 | | 9/1972 |
| EP | 0 330 254 | A | 8/1989 |
| FR | 2 091 529 | A | 1/1972 |
| FR | 2 117 625 | A | 7/1972 |
| FR | 2 124 868 | A | 9/1972 |
| FR | 2 158 401 | A | 6/1973 |
| FR | 2 179 162 | A | 11/1973 |
| GB | 1 143 759 | A | 2/1969 |
| GB | 1 247 829 | A | 9/1971 |
| GB | 1336037 | A | 11/1973 |
| GB | 1336541 | A | 11/1973 |
| JP | A-57-200355 | A | 12/1982 |

OTHER PUBLICATIONS

Oswald et al., Radical mechanisms of additions to conjugated diolefins, American Chemical Society, Division of Petroleum Chemistry, 1962, 7(3), pp. 139-152.*
Patent Abstracts of Japan, vol. 7, No. 46 (C-153), Feb. 23, 1983.
Artander, "Perfume and Flavor Chemicals", 1992.
Hofmann et al., "Quantitative Model Studies On The Effectiveness of Different Precursor Systems", Journal of Agricultural and Food Chemistry, vol. 46, 1998, pp. 235-241.

(Continued)

*Primary Examiner*—Leslie Wong
(74) *Attorney, Agent, or Firm*—Fitch Even Tabin & Flannery; Kendrew H. Colton

(57) ABSTRACT

NEW MATERIAL: A compound of formula I (R is 1~6C alkyl other than ethyl, 2~6C alkenyl).

EXAMPLE: 2-Methyl 2-mercaptopropionate.

USE: A durable flavor and taste imparting agent usable for foods, drinks, cosmetics, healthy and hygienic use, medicines, etc.

PROCESS: A 2-mercaptopropionic acid of formula II (R' is H, 1~6C alkyl or 2~6C alkenyl) is esterified with an aliphatic alcohol of the formula R'(OH) in the presence of a catalyst, e.g. an inorganic acid such as sulfuric acid or organic acid such as acetic acid, in an azeotropic solvent, e.g. benzene, at 60~100° C. to give the compound of formula I easily in high purity and yield. The molar amount of the aliphatic alcohol to be used is 1~20 times, preferably 2~5 times, that of the compound of formula II. The amount of the catalyst to be used is 0.1~10 wt % based on the compound of formula II.

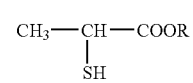

I

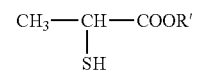

II

10 Claims, No Drawings

OTHER PUBLICATIONS

Ingles et al., "Tha Alpha-Chymotryptic Hydrolysis of Glycine Esters" Biochemical Journal, vol. 99, 1966, pp. 275-282.

Chemical Abstracts, vol. 97, No. 25, Dec. 20, 1982.

Sakaguchi et al., "Formation of Sulfur-Containing Compounds . . .", Journal of Agricultural and Food Chemistry, vol. 26, No. 5, 1978, pp. 1260-1262.

Hofmann et al., "Quantitative Model Studies On The Effectiveness of Different Precursor Systems in the Formation of the Intense Food Odorants 2-Furfurylthiol and 2-Methyl-3-furanthiol", Journal of Agricultural and Food Chemistry, vol. 46, 1998, pp. 235-241—XP-002146237.

Extract from Artander, Perfume and Flavor Chemicals, Examples 87, 876, 890, 1060, 1235, 2245 (1992)—XP-002179383.

* cited by examiner

FLAVOURING A FOODSTUFF BY INCORPORATING AN EFFECTIVE AMOUNT OF AT LEAST ONE COMPOUND OF THE FORMULA R1-S-R2 IN WHICH R1 AND R2 REPRESENT A SPECIFIC ATOM OR GROUP

CROSS-REFERENCED APPLICATIONS

This application is a National phase of International Application PCT/NL01/00279, filed 5 Apr. 2001 which designated the U.S. and that International Application was published under PCT Article 21(2) in English.

The present invention relates to flavoured foodstuffs and flavouring compositions. More in particular the present invention relates to foodstuffs having a savoury flavour and to flavouring compositions suitable for imparting or reinforcing such a flavour. Under a savoury flavour is here to be understood a flavour associated with meat, sage, poultry, cheese, mushrooms etc. The present invention, however, also relates to foodstuffs having a fruit-like or sweet, dairy flavour and to flavoring compositions suitable for imparting, reinforcing or modifying such a flavour.

The term foodstuff as used herein includes both solid and liquid ingestible materials which may or may not have nutritional value.

Flavored foodstuffs having a savoury or fruit-like flavour or fruit-like flavouring compositions for imparting to and/or enhancing in a foodstuffs a savoury or fruit-like flavour have been known for a long time, but so far these compositions were not been quite satisfactory. Therefore the present invention aims to improve the organoleptic properties of such products.

Many compounds have been used to impart a flavour to foodstuffs, in particular to impart or reinforce a savoury flavour, and therefore most of the compositions used for imparting a flavour contain a multitude of compounds. One group of particular useful compounds for savoury flavours are e.g. certain organic sulphur compounds such as thiols, sulphides and derivatives thereof like thio-acetates are e.g. disclosed and/or claimed in GB-A-1 283 912 (Unilever). GB-A-1 256 462 (International Flavours and Fragances) also discloses certain furan thiols such as 2-methylfuran-3-thiol and it derivatives such as its disulphide and other sulphides as meat flavours. More organic sulphur compounds are e.g. disclosed in "Volatile compounds in foods en beverages" by H. Maarse (ED) Marcel Dekker, N.Y. (1991), in U.S. Pat. No. 1,256,462 (International Flavours and Fragrances) and in U.S. Pat. No. 3,970,689 (International Flavours and Fragrances).

The present invention aims to improve the flavour of foodstuffs and to improve th organoleptic properties of flavour concentrates by incorporating one or more additional organic sulphur compounds as defined herein in such products. The term incorporating includes adding the actual desired compound as well as e.g. the addition of a precursor which during processing is converted into the desired compound(s).

The present invention solves the problem of obtaining more complete mild beef flavour reminiscent of beef broth, and boiled beef which is especially needed for soups, sausages, pastry etc. The same applies to fruit-like flavours, which can now also be made more complete or more "ronded of" Also by varying the relative amounts of the key components the present invention enables the flavourist to prepare flavouring compositions varying from a mild roast beef flavour to a mild beef broth flavour or to a mild to strong fruit-like flavour. Another possibility provided by the present invention is to impart or reinforce certain flavour notes by incorporating specific compounds in judicious quantities.

In a first embodiment of the present invention provides a process for flavouring a foodstuff comprising incorporating into said foodstuff an effective amount of at least one compound of the formula R1-S—R2 in which R1 and R2 represent the following combination of atoms or groups:

A. a methyl group and a 2-methyl-2-butene-1-yl group [(E)-2-methyl-1-(methylthio)-2-butene];
B. an ethyl group and a formyl group (S-ethyl thioformate);
C. an ethyl group and an 1-(3-aza-1,4-dioxo-pentyl) group (S-ethyl-2-(acetylamino)thioacetate);
D. a methyl group and a 1-(3-aza-4-oxo-pentyl) group (N-(2-methylthioethyl)acetamide);
E. a hydrogen atom and a 1-(1-methoxycarbonyl)-ethyl group (methyl2-mercaptopropionate);
F. a hydrogen atom and a 1-(1-propyloxycarbonyl)-ethyl group (propyl2-mercaptopropionate);
G. an isopropyl group and a 2-pentyl group (2-(isopropylthio)pentane);
H. a hydrogen atom and a 2-isopropenyl group (2-propenylthiol);
I. in which R1 and R2 together represent a 1-oxo-3-methyl-2-azabut-3-ene-1,4-diyl group (4-methyl-2(3H)-thiazolone) or tautomer thereof; or
J in which R1 and R2 together represent a 1,2-dimethyl-3-formyl-1,3-butadiene-1,4-diyl group (2,3-dimethyl-4-formylthiophene).

The present invention also comprises the incorporation into foodstuffs of compounds which are converted into the above mentioned compounds A through J in the foodstuff or its ingredients during storage, processing and the like (so called precursors). Examples of such compounds are e.g. esters of above identified compounds or tautomers thereof with a carboxyl-, hydroxy- or sulfhydryl group or sulfides or disulfides thereof.

The level in which the above identified compounds are incorporated depends on the nature of the compound(s), the nature of the foodstuff and in the case of a precursor on the degree of conversion into the actual flavouring compound but is generally in th range of from 1 ppb to 500 ppm by weight to 1 part by weight of foodstuff, preferably between 5 and 500 ppb. Note 1 ppb (part per billion) is here defined as 1 part by weight of flavour compound per 1 000 000 000=$10^9$ parts by weight of foodstuff, whereas 1 ppm (part per million) is here defined as 1 part of flavour compound per 1 000 000 parts by weight of foodstuff. In the case of flavouring compositions or flavour concentrate the concentration may be considerably (up to thousand to hundred thousand fold) higher. The flavouring amounts actually incorporated depend on the individual palate and on the nature of the foodstuff. Flavouring compositions can be used for enhancing or reinforcing an existing weak flavour e.g. to compensate for flavour notes lost by processing foodstuff, but they can equally be used for flavouring a bland or tasteless foodstuff. Moreover it is also possible to change the flavour characteristics of a foodstuff completely. Flavouring compositions are frequently available in the form of active material in a suspension or a solution or upon an organoleptically inactive material.

In another embodiment of the invention provides a process in which at least one compund is incorporated in which R1 and R2 represent the following combination of atoms or groups:

A. a methyl group and a 2-methyl-2-butene-1-yl group [(E)-2-methyl-1-(methylthio)-2-butene];
B. an ethyl group and a formyl group (S-ethyl thioformate);
C. an ethyl group and a 1-(3-aza-1,4-dioxo-pentyl) group [S-ethyl-2-(acetylamino)thioacetate];

D. a methyl group and a (1-3-aza-4-oxo-pentyl group(N-(2-(methylthioethyl) acetamide);

E. a hydrogen atom and a 1-(1-methoxycarbonyl)ethyl group (methyl2-mercaptopropionate);

F. a hydrogen atom and a 1-(1-propyloxycarbonyl)-ethyl group (propyl2-mercaptopropionate);

G. an isopropyl group and a 2-pentyl group (2-(isopropylthio)pentane);

H. a hydrogen atom and a 2-isopropenyl group (2-propenylthiol).

In another preferred embodiment the invention provides a process, in which at least the compound is incorporated in which R1 and R2 represent the combination of a methyl group and a 1-3-aza-4-oxo-pentyl group [N-2-(methylthioethyl)acetamide].

In another preferred embodiment the invention provides a process in which at least the compound is incorporated in which R1 and R2 represent the combination of a hydrogen atom and a methyl-2-propionate group (methyl2-mercaptopropionate).

In another preferred embodiment the invention provides a process in which at least the compound is incorporated in which R1 and R2 represent the combination of a hydrogen atom and a 2-propylenepropionate group (propyl2-mercaptopropionate).

In another preferred embodiment the invention provides a process in which the compound in which R1 and R2 represent the combination of a methyl group and a 1-3-aza-4-oxo-pentyl group [N-2-(methylthioethyl)acetamide] which is combined with 2-methyl-furan-3-thiol or a derivative or precursor thereof. As derivative or precursor of 2-methyl-furan-3-thiol are here to be understood 2-methyl-4,5-dihydrofuran-3-thiol, cis/trans 2-methyltetra-hydrofuran-3-thiol, 2-methyl-3-thiomethoxyfuran, methyl-2-methyl-3-furyldisulphide, 2-methylfuran-3-thioacetate, 2-methylfuran-3-thiopropionate and the disulphide of 2-methylfuran -3-thiol. The use of non-hydrogenated furanderivatives is preferred. Several of these compounds are available from Oxford Chemicals, Hartlepool, U.K. It is observed that 2-methylfuran-3-thiol like many other thiols is liable to oxidise partially under the influence of oxygen in the atmosphere to its disulphide and consequently quite often commercially available 2-methylfuran-3-thiol preparations contain certain amounts of its disulphide. Thioesters like 2-methyl-3-furan-3-thioacetate and e.g. 2-methyl-3-furan-3-thiopropionate may hydrolyse partially to form 2-methyl-3-furan-3-thiol under certain food processing conditions. This may apply e.g. under the conventional sterilising conditions after canning.

2-Methyl-3-furanthiol and some of its derivatives used above can be obtained or synthesized as such, but it may also be convenient to prepare e.g. a meat/beef flavour composition containing one or more of these compounds (a reaction flavour composition) which comprises at least one of these compounds in a suitable quantity and incorporate in such a composition a suitable amount of a compound having the structure R1-S—R2 as defined above. Suitable reaction flavour compositions can be prepared by reacting a hexose or pentose with a source of hydrogen sulphide such as cysteine in water as a solvent. Instead of a hexose or pentose a suitable degradation product of a sugar can be used such as e.g. 4-hydroxy-5-methyl-2,3-hydrofuran-3-one and ascorbic acid may also be used. It is also quite possible to prepare suitable reaction flavours containing 2-methyl-3-furanthiol by thermal degradation of thiamine.

Several possibilities and reaction mechanism of reaction flavours are discussed by Hoffmann & Schieberle in J. Agric. Food Chemistry, 46, 235-241 (1998) which is hereby incorporated by reference.

In another preferred embodiment the invention provides a process in which at least one of the compounds R1-S—R2 as defined above is combined with methanedithiol or a derivative or precursor thereof. Suitable derivatives and precursors are e.g methanedithiol diacetate, methylthiomethanol, methylthiomethanethiol, methylthiomethanethiol acetate, methylthiomethanethiol propionate, methylthiomethanethiol 2-methylpropionate, methylthiomethanethiol 2-methylbutanoate, methylthiomethanethiol 2-methylbutanoate, 3-methylthiomethanethiol pentanoate, methylthiomethanethiol 4-methylpentanoate and methylthiomethanethiolhexanoate. Some of these compounds are to be regarded as precursors of the corresponding free thiols, whereas others have organoleptic properties resembling methanedithiol or methylthiomethanol etc. with slightly different flavour notes. Here also the possibility arises that free thiols are partially converted to corresponding disulphides under oxidising conditions and also thioesters may hydrolyse to form free thiols under certain food processing conditions.

Generally the ratio of the amount by weight of a compound R1-S—R2 as defined above to the amount by weight of 2-methyl-furan-3-thiol or a derivative or precursor thereof and/or alternatively the amount by weight of methanedithiol or a derivative or precursor thereof ranges between 1:100 to 100:1.

In another preferred embodiment of the invention there is a process provided in which at least one compound is incorporated in which R1 and R2 together represent the one of the following groups:

A. an 1-oxo-3-methyl-2-aza-3-butene-1,4-diyl group (4-methyl-2-(3H)-thiazolone) or a tautomeric structure of the latter; or B. a 1,2-dimethyl-3-formyl-1,3-butadiene-1,4-diyl group (2,3,-dimethyl-4-formylthiophene).

In another preferred embodiment the invention provides a flavour concentrate comprising at least one compound R1-S—R2 as defined under A. to J. above, optionally in combination with methanedithiol and/or 2-methyl-furan-3-thiol or a derivative or precursor of these compounds.

A flavour concentrate for foodstuffs may be in the liquid or semi-liquid form such as solutions, emulsions or pastes, or in the dry form such as a powder. Drying can be accomplished for example by spray-drying or by freeze-drying, optionally on a carrier such as maltodextrin. As is common in flavour creation other compounds known to contribute to a specific flavour can be incorporated as well. In the case of a savoury flavour known flavouring compounds are e.g. amino acids, nucleotides, monosodiumglutamate, lower alcohols, lower carboxylic acids, pyrrolidone carboxylic acid, lower peptides, sweeteners, lactones, lower disulphides, lower thiol guanidines etc., salts like NaCl, amines, lower aldehydes, lower ketones, tricholomic acid, biotenic acid, aromatic and/or heterocyclic compounds like acetyl thiazole, 2-hydroxyethyl-4-methylthiazol, 4-hydroxy-2,5-dimethyl-2,3-hydrofuran-3-one, colouring materials, thickening agents. The proportions of these optionally added substances used are dependent on the kind of flavour desired and also on the nature of the foodstuffs in which they are incorporated and also on any herbs or spices added.

In at preferred embodiment the invention provides a flavoured foodstuff comprising at least one compound R1-S—R2 as defined under A. to J. above, optionally in combination with methanedithiol and/or 2-methyl-furan-3-thiol or a derivative or precursor of at least one of these compounds.

The invention is further illustrated by the following examples. All parts and percentages in this specification are taken on a weight basis unless otherwise indicated.

EXAMPLE 1

Synthesis of 2-methyl-1-methylthio-2-butene

To a mixture of 37 g (0.1 mole) ethylphenylphosphonium bromide in 200 mL tetrahydrofuran were 62 mL (0.1 mole) butyllithium—1.6 molar in hexane dosed at 10° C. in 15 minutes. The mixture was stirred for 15 minutes at 10° C. Subsequently 10 g (0.1 mole) methylthioacetone were dosed at this temperature during 15 minutes. The mixture was stirred without external cooling for 15 minutes. The reactioin mixture was was poured in water and extracted with hexane. The hexane extract was washed with water and dried over anh. magnesium sulphate. The solvent was evaporated until a bottom temperature of 40° C. at 4 kPa (40 mbar) was reached. The obtained precipitate (triphenyl phosphine) was removed by filtration.

The filtrate was distilled using a 5 cm Vigreux column. Obtained; 4 g distillate, b.p. 55 to 60° C. at 4.2 kPa (42 mbar). 2 g of the distillate was further purified by column chromatography (eluent: pentane: ether=95:5 v/v). Obtained; a mixture of Z and E 2-methyl-1-methylthio-2-butene=1:1.5.

Evaluation:

Beef broth 100 ppb: sulphurol, meaty, creamy, sulphury, heavy, soupy

EXAMPLE 2

Synthesis S-ethyl thioformate

Formic acid (18.8 g, 0.41 mole) was added to acetic acid (24.6 g, 0.41 mole) at room temperature. The mixture was warmed to 45° C. and kept at 45° C. for 2.5 hours. The mixture was cooled to 18° C. and pyridine (0.32 g, 0.0040 mole) was added. At 10-15° C. ethylmercaptane (12.4 g, 0.2 mole) was added during 30 minutes and the mixture was stirred at room temperature for 1 hour and then kept at that temperature for 2 days. The mixture was then poured on a barium hydroxide solution (saturated, 200 mL) and extracted with MCT oil. The organic phase was dried over potassium carbonate and then distilled. The title compound distilled at 87-92° C.

Evaluation:

Water (50 ppb): mushroom, metallic, sulphury

Water (100 ppb) mushroom, metallic, sulphury

Beef broth (1 ppm) raw ham character.

EXAMPLE 3

Synthesis of S-ethyl-2-acetylamino-ethanethioacetate

The title compound was synthesized as is disclosed by D. W. Ingles and J. R. Knowles in Biochemical Journal, 1965, 99, 275.

EXAMPLE 4

Synthesis of N-(2-methylthioethyl)acetamide

To a solution of 2-aminoethanethiol (0.2 g, 0.2 millimole) in methanol (50 g) was sodium methoxide 30% in methanol (0.44 mole) added, followed by methyliodide (0.2 mole). The mixture was stirred for two hours at room temperature. After working up 9 g distillate, b.p. 60-65° C. at 3.3 kPa (33 mbar) was obtained. To the distillate was acetic anhydride (0.1 mole) added in portions (exothermic) and the resulting solution was stirred for 15 minutes at room temperature. After working up 9 g distillate, b.p. 115° C. at 0.1 kPa (1 mbar) was obtained.

Evaluation: beef broth 100 ppb: fatty, grilled, chicken meat, sweet, beefy, heavy, enhances mouthfeel.

EXAMPLE 5

Synthesis of methyl-2-mercaptothiopropionate

A solution of 2-mercaptopropionic acid (5 g, 0.05 mole) in 50 ml methanol/0.5 g sulphuric acid was stirred for 24 hours in the presence of 20 mL mol sieves 3A. Obtained after distillation: 2.4 g methyl-2-mercaptopropionate, b.p. 64° C. at 4.8 kPa (48 mbar).

Evaluation: 0.1 ppm water: sulphury, fruity, overripe, catty, tropical

EXAMPLE 6

Synthesis of propyl-2-mercaptothiopropionate

A solution of 5 g 2-mercaptopropionic acid in 20 g propyl alcohol/0.5.g sulphuric acid was stirred for 24 hours in the presence of 20 mL mol sieves 3A. Obtained after distillation: 3.5 g propyl-2-mercaptopropionate, b.p. 80° C. at 3.5 kPa (35 mbar). Yield 47% of theory.

Evaluation 0.1 ppm water: fruity, tropical, overripe, strawberry.

EXAMPLE 7

Synthesis of 2-isopropylthiopentane

Step 1: Preparation of isopropyl-2-thiopentane.

To a solution of sodium methoxide (26.12 g; 0.16 mole) in methanol (30% w.w.) 20 ml of additional methanol was added. During stirring a solution of 2-propanethiol (11.52 g; 0.15 mole in methanol (30 ml) was added dropwise under a nitrogen atmosphere at room temperature. After the addition the reaction mixture was stirred for 20 minutes.

Step 2: Preparation of isopropyl-2-thiopentane.

To the crude mixture of step 1 above, 2-bromopentane was added dropwise at room temperature. After the addition the mixture was heated in an oil bath to a temperature of 57° C. During the reaction a white salt precipitates (NaBr). After 30 minutes of reaction the mixture was cooled and kept under nitrogen at 20° C. overnight.

During evaporation of the methanol using a Rotavapor more salt precipitates. This indicates that the reaction had not gone to completion. After 1.5 hours at 60° C. water was added to the mixture. The mixture was then extracted wit diethylether (3×100 ml). The organic layer was washed with a dilute sodium hydroxide solution to remove any remaining 2-propanethiol. Afterwards the diethyl layer was washed three times with with 100 ml of water and dried over anhydrous magnesium sulphate. After filtration the ether was evaporated using a Rotavapor.

The crude product was distilled. Two main fractions were collected. A mixture of these two was analyzed by NMR and it was concluded was the desired product had been formed, but still contained 20% of an unknown impurity. The most pure fraction of 7.3 g (0.05 mole), yield 33% was analysed with GC-MS and found suitable for flavouring purposes.

Evaluation in water: 100 ppb: fruity, floral sulphury, sweet.

EXAMPLE 8

Synthesis of 2-mercaptopropene

The synthesis of 2-mercaptopropene (an orange oil) through hydrolysis of 2,2-dimercaptopropene, as is disclosed by R. D. Lipscombe, W. H. Sharkey in Journal of Polymer Science A-1, 1970, 8, 2187

EXAMPLE 9

Synthesis of 4-methyl-2-(3H)-thiazolone

A solution of the following reagents was prepared: in a conical flask:

| | |
|---|---|
| Monochloroacetone | 9.25 g (0.1 mole) |
| Potassium thiocyanate | 12.5 g (0.13 mole) |
| Sodiumhydrogen carbonate | 3 g (0.03 mole) |
| Water | 150 ml. |

The solution was left to react at room temperature for 48 hours and then stirred for 12 hours.

The solution turned from colourless into a yellow solution with a brown oily sediment.

The mixture was filtered and the water layer was heated for 45 minutes at 50° C. Activated carbon was added and the mixture was stirred at room temperature for two hours. The carbon was then filtered off and the water was evaporated using a Rotavapor. A white solid precipitates when enough water was evaporated, it was filtered off and the mother liquor was kept in the freezer overnight. After slowly reaching room temperature a large amount of product had crystallised and was filtered off. It could be recrystallised by adding 5 times the amount of water (w.w.), dissolving at 50-55° C. and slowly cooling. Yield 0.97 g (8 mmoles; 8%). The product was analysed by NMR and found to be pure.

Evaluation: water, 100 ppb: fatty, mealy, sulphury, mushroom, boiled beef notes.

EXAMPLE 10

Synthesis of 2,3,-dimethyl-4-thiophenealdehyde

The synthesis of 2,3,-dimethyl-4-thiophenealdehyde is disclosed in A. Wiersema in Acta Chem. Scand. 1970, 24, 2593. Its b.p. is 103-106° C., $^1$HNMR (CDCl$_3$): 9.77,7.75, 2.3.

EXAMPLE 11

Four savoury flavour compositions were prepared by mixing the following ingredients in the amounts (parts per thousand) indicated in the table below in t=trans and c=cis: The four mixtures A, B, C and D so obtained were added separately to a test solution (50° C. containing 5 g/L sodium chloride) at a level of 0.04 g per liter. The flavoured test solutions were evaluated by a panel of four experienced tasters. Three of the four tasters preferred mixtures B, C and D over mixture A.

| Compound | Mixt. A | Mixt. B | Mixt. C | Mixt. D |
|---|---|---|---|---|
| Hexanal | 11.4 | 11.4 | 11.4 | 11.4 |
| Nonanal | 2.0 | 2.0 | 2.0 | 2.0 |
| t-2-Heptenal | 1.2 | 1.2 | 1.2 | 1.2 |
| t-2-Octenal | 1.2 | 1.2 | 1.2 | 1.2 |
| t-2-Nonenal | 1.2 | 1.2 | 1.2 | 1.2 |
| t-2-Decenal | 3.5 | 3.5 | 3.5 | 3.5 |
| t,t-2,4-Heptadienal | 1.0 | 1.0 | 1.0 | 1.0 |
| t,t-2,4-Nonadienal | 0.8 | 0.8 | 0.8 | 0.8 |
| t,t-2,4-Decadienal | 20.8 | 20.8 | 20.8 | 20.8 |
| (2-Hydroxyethyl)-4-methyl-thiazol | 947.8 | 947.8 | 947.8 | 947.8 |
| 1-Octene-3-ol | 0.6 | 0.6 | 0.6 | 0.6 |
| 1-Hexanol | 3.6 | 3.6 | 3.6 | 3.6 |
| δ-Undecalactone | 0.6 | 0.6 | 0.6 | 0.6 |
| 2-Ethyl-1-hexanol | 0.5 | 0.5 | 0.5 | 0.5 |
| 2-Methyl-3-furanthiol | — | — | — | 1.3 |
| 2-Methyl-1-(methylthio)-2-butene | — | 2.5 | 2.5 | — |
| N-(2-methylthioethyl) acetamide | — | — | — | 2.5 |
| Ethanol (up to 1000) | 3.8 | 1.3 | 1.3 | 0.0 |

The invention claimed is:

1. A process for flavoring a foodstuff comprising incorporating into said foodstuff a flavoring effective amount of 2-methyl-1-methylthio-2-butene.

2. The process according to claim 1, wherein the flavoring further includes incorporating a combination of 2-methyl-1-methylthio-2-butene and propyl-2-mercaptopropionate.

3. The process according to claim 1, wherein the flavoring further includes incorporating a combination of 2-methyl-1-methylthio-2-butene and 2-methyl-furan-3-thiol or a compound selected from the group consisting of 2-methyl-4,5-dihydrofuran-3-thiol, cis/trans 2-methyltetra-hydrofuran-3-thiol, 2-methyl-3-thiomethoxyfuran, methyl-2-methyl-3-furyldisulphide, 2-methylfuran-3-thioacetate, 2-methylfuran-3-thiopropionate, and the disulphide of 2-methylfuran-3-thiol.

4. The process according to claim 1, wherein the flavoring further includes incorporating a combination of 2-methyl-1-methylthio-2-butene with methanedithiol or a compound selected from the group consisting of methanedithiol diacetate, methylthiomethanol, methylthiomethanethiol, methylthiomethanethiol acetate, methylthiomethanethiol propionate, methylthiomethanethiol 2-methylpropionate, methylthiomethanethiol 2-methylbutanoate, 3-methylthiomethanethiol pentanoate, methylthiomethanethiol 4-methylpentanoate and methylthiohexanoate.

5. The process according to claim 1, wherein the flavoring imparts a savory flavor to said food stuff.

6. A flavor concentrate for flavoring a foodstuff comprising 2-methyl-1-methylthio-2-butene.

7. The flavor concentrate according to claim 6, wherein in the flavor concentrate comprises 2-methyl-1-methylthio-2-butene in combination with 2-methyl-furan-3-thiol and/or methanedithiol or a compound selected from the group consisting of 2-methyl-4,5-dihydrofuran-3-thiol, cis/trans 2-methyltetra-hydrofuran-3-thiol, 2-methyl-3-thiomethoxyfuran, methyl-2-methyl-3-furyldisulphide, 2-methylfuran-3-thioacetate, 2-methylfuran-3-thiopropionate, the disulphide of 2-methylfuran-3-thiol, methanedithiol diacetate, methylthiomethanol, methylthiomethanethiol, methylthiomethanethiol acetate, methylthiomethanethiol propionate, methylthiomethanethiol 2-methylpropionate, methylthiomethanethiol 2-methylbutanoate, 3-methylthiomethanethiol pentanoate, methylthiomethanethiol 4-methylpentanoate and methylthiohexanoate.

8. A flavored foodstuff comprising a foodstuff flavored with a flavoring effective amount of 2-methyl-1-methylthio-2-butene.

9. The flavored foodstuff according to claim 8, wherein said 2-methyl-1-methylthio-2-butene is combined with at least one of 2-methyl-furan-3-thiol, methanedithiol or a compound selected from the group consisting of 2-methyl-4,5-dihydrofuran-3-thiol, cis/trans 2-methyltetra-hydrofuran-3-thiol, 2-methyl-3-thiomethoxyfuran, methyl-2-methyl-3-furyldisulphide, 2-methylfuran-3-thioacetate, 2-methylfuran-3-thiopropionate, the disulphide of 2-methylfuran-3-thiol, methanedithiol diacetate, methylthiomethanol, methylthiomethanethiol, methylthiomethanethiol acetate, methylthiomethanethiol propionate, methylthiomethanethiol 2-methylpropionate, methylthiomethanethiol 2-methylbutanoate, 3-methylthiomethanethiol pentanoate, methylthiomethanethiol 4-methylpentanoate and methylthiohexanoate.

10. The flavored foodstuff according to claim 8, wherein said foodstuff receives a savory flavor from being flavored with said flavoring effective amount.

\* \* \* \* \*